United States Patent [19]

So et al.

[11] Patent Number: 5,674,506
[45] Date of Patent: Oct. 7, 1997

[54] MAKE-UP COSMETIC COMPOSITIONS CONTAINING POWDERED PHAFFIA YEAST

[75] Inventors: Sung So; Yong Ki Kim; Do Keun Park, all of Suwon; Yeo Ran Yun, Seongnam, all of Rep. of Korea

[73] Assignee: Pacific Corporation, Seoul, Rep. of Korea

[21] Appl. No.: 398,573

[22] Filed: Mar. 3, 1995

[30] Foreign Application Priority Data

Mar. 4, 1994 [KR] Rep. of Korea ............. 1994-4186

[51] Int. Cl.$^6$ .............. A61K 6/00; A61K 7/00
[52] U.S. Cl. .............. 424/401; 424/63; 424/450
[58] Field of Search .............. 424/450, 401, 424/63; 435/255.1, 67; 514/844, 845

[56] References Cited

FOREIGN PATENT DOCUMENTS 0454024  4/1991  European Pat. Off. .

OTHER PUBLICATIONS

Okagbue et al., Influence of mixed culture conditions on yeast-wall hydrolytic activity of Bacillus circulans WL-12 and on extractability of astaxanthin from the yeast Phaffia rhodozyma, vol. 59(3), (1985), pp. 243–255. (Exhibit B).

*Primary Examiner*—Thurman K. Page
*Assistant Examiner*—Sharon Howard
*Attorney, Agent, or Firm*—John P. White

[57] ABSTRACT

Disclosed herein is make-up cosmetic compositions containing powdered Phaffia yeast.

According to the present invention, the make-up cosmetic composition contains the powdered Phaffia yeast in an amount of 0.1 to 50% by weight based on the total amount of the composition. Said powdered Phaffia yeast is prepared by sterilizing Phaffia yeast by radiation sterilization or compressed steam sterilization, and then spray-drying the suspension containing the sterilized yeast. The Phaffia yeast employed in the present invention are *Phaffia rhodozyma*, astaxanthin-producing mutants, β-carotane-accumulating mutants and white carotenoid pigments-producing mutants, of *Phaffia rhodozyma*. Because the make-up cosmetics according to the present invention employ the Phaffia yeast including its cell contents, they can provide the preference of using the active contents of the yeast without the complicated pre-treatment, which have been indispensable in the prior art, and exhibit excellent effects on color-expressions, color-retention, feel and spreadability, compared with the conventional compositions.

5 Claims, No Drawings

MAKE-UP COSMETIC COMPOSITIONS CONTAINING POWDERED PHAFFIA YEAST

BACKGROUND OF THE INVENTION

1. Fields of the Invention

The present invention is related to make-up cosmetic compositions, and more particularly is related to make-up cosmetic compositions containing powdered Phaffia yeast, which exhibit excellent color-expressions, feel and spreadability.

2. Prior Art

Phaffia yeast contains rich lipids, mainly composed of unsaturated fatty acids. Further, it contains rich astaxanthin (3,3'-dihydroxy-carotene-4,4-dione) having an excellent anti-oxidation activity. Because astaxanthin contained in Phaffia yeast is pink pigment, this yeast has been named "Red yeast".

Yeasts have been employed in producing make-up cosmetic compositions. For example, a make-up cosmetic composition containing the polysaccharide powder of yeasts has been known to show excellent color-expressions, feel, spreadability, when it is applied to the skin. The polysaccharide powder is prepared from *Saccharomyces cerevisias* by removing the contents of the cell to give cell wall, which is then subjected further treatments. However, in spite of said excellent properties, the polysaccharides may not be employed widely in the preparation of cosmetics, because said polysaccharide powder of the yeast must be treated with a complicated process which comprises the steps of impregnating organic and inorganic pigments and silica into the powder and then coating the powder with a water-soluble polymer.

Accordingly, there has been a need to find out a solution having no problems as described above and may be directly applied to the cosmetic compositions without said complicated pre-treatments.

Under these circumstances, the present inventors have conducted extensive studies to find out yeasts satisfying said need and to provide a method for applying the active contents of the yeast to the cosmetics. As a result, we found that the above objective can be accomplished by using the powdered Phaffia yeast. In other words, the powdered Phaffia yeast can be applied to make-up cosmetics without said complicated pretreatment treatment, including an impregnation of pigments and a coating with polymers. When the make-up cosmetics containing powdered Phaffia yeast are applied to the skin, there may be obtained improved color-expressions, feel and spreadability without the irritation to the skin. Further, the cosmetics show a good sun-screening action. Based on these findings, the present invention has been accomplished.

SUMMARY OF THE INVENTION

Thus, an object of the invention is to provide make-up cosmetic compositions containing powdered Phaffia yeast, which show excellent color-expressions, feel and spreadability.

DETAILED DESCRIPTION OF THE INVENTION

Phaffia yeast used in the present invention contains a larger amount of lipids, mainly composed of unsaturated fatty acids than the other yeasts. Further, it contains rich astaxanthin having an excellent anti-oxidation activity. Phaffia yeast containing rich nutrients may be served as an ingredient in cosmetics as it is. For this purpose, the Phaffia yeast can be used after only drying and powdering process, without removing its cell contents. The following tables 1 and 2 show the type and contents of various nutrients, and particularly, fatty acids contained in conventional baker's yeast and Phaffia yeast of the present invention.

TABLE 1

The nutrients contained in baker's yeast and phaffia yeast

| Nutrients | Phaffia yeasts (Phaffia rhodozyma) | Baker's yeast (Saccharomyces cervisiane) |
|---|---|---|
| Ash | 9.6 | 9.9 |
| Carbohydrate | 40.3 | 33.4 |
| Crude protein | 28.9 | 46.9 |
| Nucleic acid | 8.2 | 9.2 |
| Fat | 17.0 | 4.0 |
| Astaxanthin | 0.06 | 0.0 |

TABLE 2

Fatty acids contained in baker's yeast and phaffia yeast

| No. of Carbon: No. of Double bonds | Fatty acids | Phaffia yeast | Baker's yeast |
|---|---|---|---|
| 14:0 | Myristic acid | 0.24 | 13.0 |
| 16:0 | Palmitic acid | 16.05 | 9.8 |
| 16:1 | Palmitoleic acid | 0.45 | 58.6 |
| 18:0 | Stearic acid | 6.11 | 2.1 |
| 18:1 | Oleic acid | 41.3 | 26.6 |
| 18:2 | Linoleic acid | 32.8 | 0.9 |
| 18:3 | Linolenic acid | 3.0 | 0.0 |

The powdered Phaffia used in the present invention may be prepared by a conventional technique which is known to the skilled in the art. In detail, yeast may be cultivated under the conventional cultivation conditions, and then be isolated from the culture broth, sterilized, dried and finally powdered.

In case that the living yeast is added to the cosmetics, the cosmetics may cause the irritations to the skin due to the metabolites of the yeast. Accordingly, for the use of the Phaffia yeast in the cosmetics, the sterilization is inevitable step. For sterilizing the Phaffia yeast in the present invention, any conventional sterilizations, for example, a steam sterilization at a high pressure, at 121° C., or a radiation sterilization may be employed. After sterilization, cells are completely killed, while astaxanthin and unsaturated fatty acids contained therein are not destructed.

In drying thus sterilized yeast, it is likely to coagulate each other, resulting in the rough surface of the particles and poor feel of the cosmetics containing this particles very poor. The present inventors tried to solve this problem and found that spray-drying method can be employed for this purpose without any coagulation. In this method, the sterilized yeast may be suspended in water to a concentration of 20%(dry weight/volume) or less, and spray-dried to give powder. In the present invention, the Phaffia yeast obtained by this method is named "powdered Phaffia yeast", in distinction from Phaffia yeast itself.

As the yeast of Phaffia genus, there is only species, *Phaffia rhodozyma*, which is available from American Type Culture Collection; ATCC). The present invention can employ any one species of *Phaffia rhodozyma* ATCC 24201, 24202, 34303, Z4228, 24229, 24230, 24261, 66270 and 66272, and preferably, ATCC 66272 having a high level of astaxanthin. Because these strains were not deposited for the purpose of patents, they are available to the public without no limitation.

However, the present invention is not limited to said strains and can employ the mutants derived from these strains or any wild type of *Phaffia rhodozyma*. For example, astaxanthin-producing mutants, β-carotene-accumulating mutants, white carotenoid pigments-producing mutants and the like also may be employed.

The powdered Phaffia yeast prepared in the above, can be incorporated in the conventional make-up cosmetics, in an amount of 0.1 to 50% by weight based on the total amount of the composition, preferably 1 to 30% by weight, which is not limited and can be chosen depending on the formulations or the final purpose of the cosmetics.

PREFERRED EMBODIMENT OF THE INVENTION

The present invention will be described in more detail by way of the following non-limiting Examples.

EXAMPLE 1

The preparation of the powdered Phaffia yeast (1)

In a 3000 liters of the fermentor containing 2000 liters of YM medium [0.3% of yeast extract, 0.3% of malt extract, 0.5% of peptone, 1.0% of dextrose, pH 5.0; Sacto YM Broth, Difco Laboratories, U.S. A], 20 liters of the yeast of *Phaffia rhodozyma* ATCC 66272, which had been cultured in the Same medium for 4 days, was inoculated and cultured at 22° C., under shaking at 100 RPM for about 4 days with aeration of 1.0 VVM. After culture was completed, broths were centrifuged at the rate of 10,000 X g and then the isolated call pellets were washed with distilled water.

The cells were isolated by centrifugation, dried under the reduced pressure, and sterilized by 6 Kgray of gamma rays.

The sterilized cells were suspended in distilled water to a concentration of 10%(dry weight/volume), and then spray-dried to give 15kg of the powdered Phaffia yeast.

EXAMPLE 2

The preparation of the powdered Phaffia yeast (2)

The cultivation was carried out by the same procedure as described in Example 1. The obtained broths were sterilized by flowing the compressed steam, of which the temperature is 121° C., into the fermentor containing said culture.

The sterilized cells were suspended in distilled water to a concentration of 10%(dry weight/volume), and then spray-dried to give 15 kg of the powdered Phaffia yeast.

Formulation 1 and Comparative Formulations 1-2 : Compact

Of the following table 3, materials 8 to 10 were melted by heating to 50°–60° C., and then materials 1 to 7 were dispersed therein. The mixture was sprayed and grinded.

TABLE 3

| Compact Formulations | | | |
|---|---|---|---|
| Ingredients | *F. 1 | **C.F. 1 | [% by weight] C.F. 2 |
| 1. Sericite | to 100 | to 100 | to 100 |
| 2. Mica | 20.0 | 20.0 | 20.0 |
| 3. Titanium dioxide | — | — | 1.0 |
| 4. Yellow ferric oxide | — | — | 0.5 |

TABLE 3-continued

| Compact Formulations | | | |
|---|---|---|---|
| Ingredients | *F. 1 | **C.F. 1 | [% by weight] C.F. 2 |
| 5. Ferric oxide | — | — | 0.5 |
| 6. The powdered Phaffia yeast (Example 1) | 3.0 | — | — |
| 7. Polysaccharide of the yeast | — | 3.0 | — |
| 8. Liquid paraffin | 5.0 | 5.0 | 5.0 |
| 9. Perfume | 0.2 | 0.2 | 0.2 |
| 10. Preservative | 0.1 | 0.1 | 0.1 |

(Notes)
*F.: Formulation
**C.F.: Comparative Formulation

Formulation 2 and Comparative Formulation 3: W/O type Cream foundation

Of the following table 4, materials 1 to 7 were halted by heating to 85°–90° C., materials 8 to 13 were added thereto and then stirred for 30 minutes. Material 13 was mixed with material 14 while heating to 73° C., end then this mixture was added to said mixture under stirring for 30 minutes, and cooled to 30° C.

TABLE 4

| W/O type Cream foundation formulations | | |
|---|---|---|
| Ingredients | *F. 2 | [% by weight] **C.F. 3 |
| 1. Bee wax | 6.0 | 6.0 |
| 2. Ceresin | 2.0 | 2.0 |
| 3. Liquid paraffin | 25.0 | 25.0 |
| 4. Lanoline | 2.0 | 2.0 |
| 5. Sorbitan monostearate | 3.0 | 3.0 |
| 6. Perfume | 0.2 | 0.2 |
| 7. Preservative | 0.2 | 0.2 |
| 8. Titanium dioxide | 5.0 | 10.0 |
| 9. Ferric oxide | — | 0.4 |
| 10. Yellow ferric oxide | — | 1.0 |
| 11. Black ferric oxide | — | 0.2 |
| 12. The powdered Phaffia yeast (Example 2) | 5.0 | — |
| 13. Magnesium sulfate | 0.5 | 0.5 |
| 14. Distilled water | to 100 | to 100 |

(Notes)
*F.: Formulation
**C.F.: Comparative Formulation

Formulation 3 and Comparative Formulation 4: Lipstick

Of the following table 5, oil and wax materials were melted by heating to 80°–85° C., and then pigments were dispersed therein for 30 minutes. The dispersion was degassed and perfume was added thereto. The mixture was stirred.

TABLE 5

| Lipstick formulations | | |
|---|---|---|
| Ingredients | *F. 3 | [% by weight] **C.F. 4 |
| 1. Cantor oil | to 100 | to 100 |
| 2. Ceresin | 5.0 | 5.0 |
| 3. Canderilla wax | 11.0 | 11.0 |
| 4. Hard wax | 3.0 | 3.0 |
| 5. Capric/Caprylic triglyceride | 10.0 | 10.0 |
| 6. Diisostrearyl malate | 4.0 | 4.0 |

TABLE 5-continued

Lipstick formulations

| Ingredients | *F. 3 | [% by weight] **C.F. 4 |
|---|---|---|
| 7. Isotridecyl isononanoate | 0.5 | 0.5 |
| 8. Ferric oxide | 0.3 | 0.3 |
| 9. Aluminum lake Red No. 201 | — | 0.3 |
| 10. Yellow ferric oxide | — | 1.5 |
| 11. Mica titanium | 10.0 | 10.0 |
| 12. The powdered phaffia yeasts (Example 1) | 2.0 | — |
| 13. Perfume | 0.2 | 0.2 |

(Notes)
*F.: Formulation
**C.F.: Comparative Formulation

Experimental Example Effects of cosmetic compositions containing the powdered Phaffia yeast on the skin In order to evaluate the effects of make-up cosmetic compositions containing the powdered Phaffia yeast on the skin. Compact, W/O type cream foundation and lipstick formulations, prepared in Formulations 1 to 3 and Comparative Formulations 1 to 4, were estimated for color-expression, color-retention ability, feel and spreadability.

30 females aging 20 to 30 were applied the inventive composition (Formulations 1 to 3) on the left side of the face and the conventional composition (C. Formulations 1 to 4) on the right side of the face at a.m. 10 o'clock. After 5 hours, i.e. at p.m. 3 o'clock, for color-expression, color retention ability, feel and spreadability, the subject choose the preferred of the two compositions tested on the subject. The evaluation was carried out for ten days in order to provide a reliability. For each effect, 1 point was given for the chosen composition and 0 for the other(s) by each subject and the average for ten days was taken. The results are shown in Tables 6 to 8.

TABLE 6

Compact

| | Color-expression | Color-retention | Feel | Spreadability |
|---|---|---|---|---|
| * F. 1 | 19 | 20 | 21 | 20 |
| ** C.F. 1 | 8 | 7 | 6 | 8 |
| C.F. 2 | 3 | 3 | 3 | 2 |

(Notes)
*F.: Formulation
**C.F.: Comparative Formulation

TABLE 7

W/O type cream foundation

| | Color-expression | Color-retention | Feel | Spreadability |
|---|---|---|---|---|
| * F. 2 | 20 | 21 | 23 | 20 |
| ** C.F. 3 | 10 | 9 | 7 | 10 |

(Notes)
*F.: Formulation
**C.F.: Comparative Formulation

TABLE 8

Lipstick

| | Color-expression | Color-retention | Feel | Spreadability |
|---|---|---|---|---|
| * F. 3 | 19 | 26 | 20 | 22 |
| ** C.F. 4 | 11 | 4 | 10 | 8 |

(Notes)
*F.: Formulation
**C.F.: Comparative Formulation

As shown in above Experimental Example, the make-up cosmetic compositions containing the powdered Phaffia yeast exhibit excellent effects on color-expression, color-retention, feel and spreadability, compared with the conventional compositions. Further, because the make-up cosmetic compositions according to the present invention employ the Phaffia yeast including its cell contents, they can provide the preference of using the active contents of the yeast without the complicated pre-treatment, which have been indispensable in the prior art.

What is claimed is:

1. A composition comprising:
   a cosmetic base selected from liquid paraffin or castor oil; and
   powdered Phaffia yeast,
   wherein said yeast is prepared by sterilizing Phaffia yeast, and suspending it in distilled water to a concentration of 20% (dry weight/volume) or less, and then spray-drying the suspension.

2. The composition as claimed in claim 1, further comprising one or more pigments for make-up cosmetics.

3. The composition as claimed in claim 1, wherein the Phaffia yeast is suspended as a whole cell.

4. The composition as claimed in claim 1, wherein Phaffia yeast is any one selected from the group consisting of *Phaffia rhodozyma*, and astaxanthin-producing mutants, B-carotene-accumulating mutants and white carotenoid pigments-producing mutants, of *Phaffia rhodozyma*.

5. The composition as claimed in claim 1, wherein the powdered Phaffia yeast are present in an amount of 0.1 to 50% by weight based on the total amount of the composition.

* * * * *